United States Patent [19]

Whitehead et al.

[11] Patent Number: 4,642,230
[45] Date of Patent: Feb. 10, 1987

[54] RELEASE DEVICE

[75] Inventors: Derek J. Whitehead, Poynton; Michael T. Shepherd, Cheddington, both of England

[73] Assignees: Castex Products Limited, Macclesfield; The Wellcome Foundation Limited, London, both of England

[21] Appl. No.: 736,555

[22] Filed: May 21, 1985

[30] Foreign Application Priority Data

Jun. 2, 1984 [GB] United Kingdom ............... 8414123
Aug. 31, 1984 [GB] United Kingdom ............... 8422093
Mar. 2, 1985 [GB] United Kingdom ............... 8505410

[51] Int. Cl.$^4$ .................... A01N 25/34; A61K 9/22; A61K 9/26
[52] U.S. Cl. ........................ 424/15; 424/14; 424/16; 424/19; 424/21; 424/22; 604/890; 604/892
[58] Field of Search ............ 424/14, 16, 19, 22, 424/15, 21; 604/890, 892

[56] References Cited

U.S. PATENT DOCUMENTS

| D. 14,842 | 3/1884 | Griscom | D28/2 |
|---|---|---|---|
| 2,928,770 | 3/1960 | Bardani | 424/22 |
| 3,056,724 | 10/1962 | Marston | 424/22 |
| 3,228,789 | 1/1966 | Glassman | 424/19 |
| 3,567,818 | 3/1971 | Hemingway et al. | 424/14 |
| 3,594,469 | 7/1971 | Whitehead et al. | 424/14 |
| 3,964,438 | 6/1976 | Rodemeyer | 426/132 |
| 4,308,250 | 12/1981 | Griffin et al. | 424/14 |
| 4,381,780 | 5/1983 | Holloway | 604/892 |
| 4,439,196 | 3/1984 | Higuchi | 604/890 |
| 4,449,981 | 5/1984 | Drake et al. | 604/890 |
| 4,475,916 | 10/1984 | Himmelstein | 604/890 |
| 4,552,751 | 11/1985 | Inaba et al. | 424/19 |

FOREIGN PATENT DOCUMENTS

| 942667 | 2/1974 | Canada | 424/14 |
|---|---|---|---|
| 3336615 | 4/1985 | Fed. Rep. of Germany | 604/890 |
| WO82/00094 | 1/1982 | PCT Int'l Appl. | 604/890 |
| 1603970 | 12/1981 | United Kingdom | 604/890 |
| 2020181 | 2/1983 | United Kingdom | 424/14 |
| 2115073 | 9/1983 | United Kingdom | 604/890 |

Primary Examiner—Ronald W. Griffin
Attorney, Agent, or Firm—Donald Brown; Robert T. Gammons

[57] ABSTRACT

A bolus for administering a biologically active material for example an insecticide into a liquid environment such as the water of a reservoir or lake or an anthelmintic into the rumen juices of an animal comprises a succession of liquid impermeable outer segments (153, 263) enclosing a core which in the simplest case may be a single unitary active material segment (151, FIG. 14) or in a developed embodiment may comprise a succession of annular segments (269, FIG. 25) contained in sealed recesses (267) in the outer segments (263) which are located on a degradable central rod (265) e.g. of magnesium alloy, which itself will be active for instance to combat magnesium deficiency.

As shown in FIG. 25, the device may incorporate a weight (275) which, in animal use, inhibits regurgitation. Additionally, the device may include a galvanic couple element which, with the rod (265) sets up a galvanic action which controls the speed of degradation of the rod (265) and thereby the rate of administration of the segments (26).

20 Claims, 34 Drawing Figures

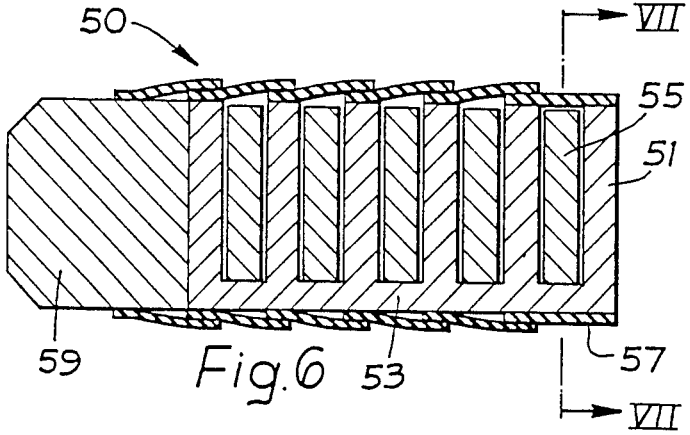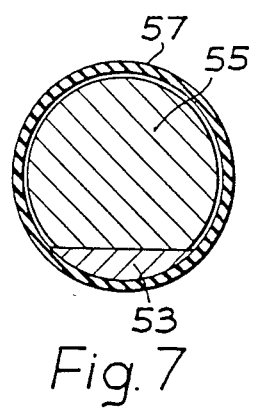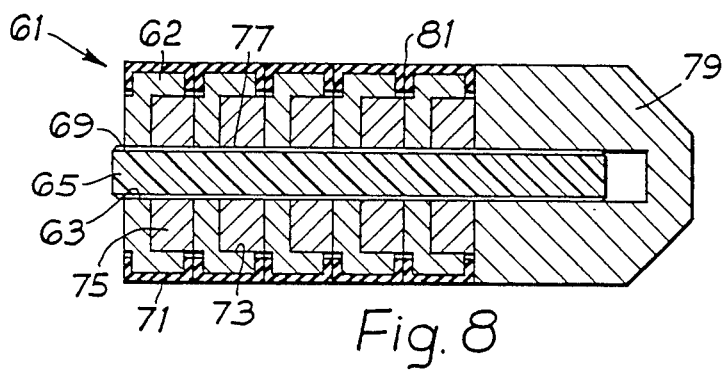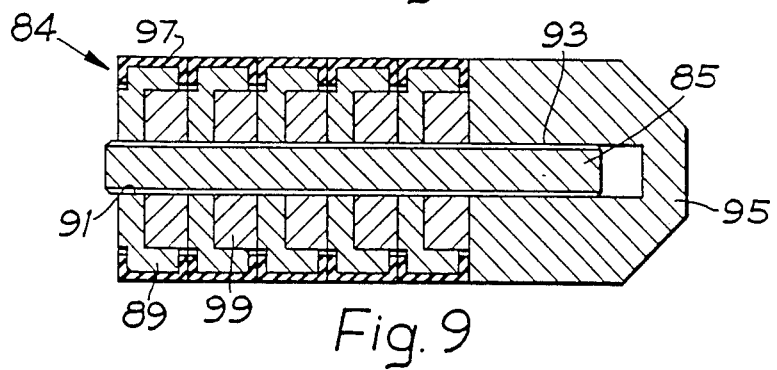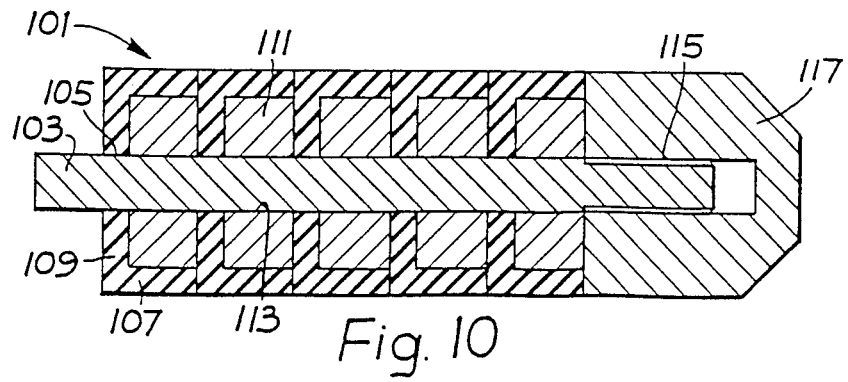

RELEASE DEVICE

The present invention relates to release devices for releasing substances into liquid environments, for example into body fluids of animals or humans, or into rivers, lakes or the like.

The invention is more particularly concerned with a release device, as aforesaid, which is in the form of a generally elongate bolus having two ends and comprising a degradable core, which consists of or contains a biologically active material, surrounded by a liquid impermeable casing except at one of its ends or both of its ends.

Various devices are known for the gradual release of an anthelmintic or a trace element into the rumenoreticular sac of a ruminant animal over a prolonged period. One such device is described in U.K. Patent Specification No. 1 603 970. In the latter device, a precast cylindrical plug containing a therapeutic composition of anthelmintic is housed in a tubular body and urged by a spring toward a restricted opening at one end thereof. The end of the plug adjacent to the restricted opening disintegrates as it contacts the rumenal fluids. One disadvantage of this arrangement is that the opening can become blocked with grass or other matter present in the rumen, thereby impeding the release of the composition at a steady rate. Another problem with the device is that insufficient sealing between the plug and the tubular body can allow the ingress of fluid, resulting in irregular disintegration of the plug with consequent variation in the release of anthelitintic.

The device described above may be equipped with protruding wings of a plastics material to prevent it from being regurgitated by the animal. An alternative means of preventing regurgitation of such a device is to make it sufficiently dense. An intra-rumenal device which relies on overall density to ensure retention is described in U.K. Patent Specification No. 2 020 181. This device contains a therapeutic composition in a weighted tube, the ends of which are closed each by a porous member impregnated with a hydrogel material. When the device is located in the rumen, the therapeutic composition is gradually released through the porous end pieces. Since release of the composition depends on osmosis, as the amount of composition in the device progressively reduces during use, so the rate of release progressively decays. This can be a disadvantage where a constant rate of administration of composition to the animal is required.

For both of the devices described above, when the therapeutic agent is exhausted, the body of the device is retained in the animal. Not only is this generally regarded as disadvantageous by farmers, but the body of the device remains in the carcass after slaughter and can damage machinery used in the subsequent processing of the carcass.

Additionally, with both of the above-described known devices, the therapeutic composition is released more or less continuously until it is exhausted. However when it is desired to administer an anthelmintic in this way, if for any reason the amount of anthelmintic released is insufficient to kill all of the helminths, a resistance to the agent can be produced in subsequent generations. Therefore, it is now believed to be desirable for the anthelmintic to be released from an intra-rumenal device in "pulsed doses", that is to say in a plurality of doses between which there is substantially none of the agent present in the rumenal fluids. This includes instances where, for example, in a period when substantially none of a previously-released dose is present, the device releases a subsequent dose, e.g. of a different anthelmintic or another biologically active substance.

We have now devised a bolus which is particularly, but not exclusively, suitable for use as an intra-rumenal device and which, in each of its various embodiments, overcomes one or more of the disadvantages indicated for both of the devices described above. For intra-rumenal use, such a device can be constructed for continuous or pulsed release administration (or both simultaneously) as desired. The bolus may also be used in other applications such as the administration of therapeutic, nutrient and other agents to humans and animals, and for the release of agents such as insecticides, aquatic herbicides and fish nutrients and vaccines into rivers, reservoirs, lakes, ponds, pools (including swimming pools) or tanks, or the like.

The present invention provides a release device in the form of a generally elongate bolus having two ends and a core comprising one or more degradable inner segments, at least one of which consists of or contains a biologically active component, the core being surrounded by a liquid impermeable casing, said casing comprising a plurality of outer segments such that the outer segments together form the liquid-impermeable casing surrounding the core which is exposed at one or both of the ends of the bolus.

The construction of the bolus may be such that, in use, the inner segment or segments which constitute the core are successively degraded from one or both ends of the bolus, which thereby releases the biologically active material, and the outer segments are successively shed from the bolus.

The inner segment or segments of the core of bolus according to the present invention are degradable in that they can be degraded when exposed to the liquid environment in which the bolus is placed during use. Such degradation may occur by one or more actions of the liquid environment, or a component thereof, on the inner segments. Such actions include chemical reactions between the inner segments and the liquid (i.e. by corrosion), the action of microorganisms such as bacteria (i.e. biodegradation), the dissolving of the inner segment in the liquid, and also abrasion. Similarly, the outer segments are substantially inert when exposed to the said liquid environment. It will be appreciated that the degradation of the inner segments may be effected by the liquid or a component thereof on only one or some of the components of said inner segments, this being sufficient to cause a breakdown of the inner segment structure.

When there is a plurality of inner segments, these may be of the same material as one another or of different materials, provided that each of the materials is degradable as described above. Two or more inner segments may be interspersed by inert flange members extending inwardly from the inert outer segments and may serve to hold the bolus together, for example by locking onto a central rod as described further hereinbelow. In some embodiments, there may be two or more types of inner segments, respectively of different degradable materials. The latter materials may each include at least one biologically active component, although not necessarily the same biologically active component as one another.

Alternatively, for example, one of the materials may contain a biologically active component and the other may be a degradable material containing substantially no biologically active component. Generally, when there are just two types of inner segments, the segments of the two types may be arranged alternately in the core. Thus, when inner segments of one type contain substantially no biologically active component, such segments act as spacers between the inner segments of the other type, that is the inner segments containing a biologically active component. This is particularly advantageous when the bolus is intended for pulsed release administration. Inner segments which are of the same material as one another may be interconnected by a peripheral spine running longitudinally within the casing formed by the outer segments and preferably integral with the inner segments.

In embodiments where there is only a single or unitary inner segment, this will of course constitute substantially the whole of the core. In embodiments where the liquid impermeable casing does not cover either end of the bolus, the inner segments may be so arranged that in use, one or more biologically active components may be released alternately from each end. For example, a first component may be released from one end after a period of (say) 21 days from first use and then a second component may be released from the other end after a further period of 21 days, and so on alternately. Of course, pulsed or continuous release of the same or one or more other biologically active component(s) may proceed simultaneously from both ends in this manner.

Thus, differently expressed, the present invention provides a generally elongate bolus having two ends and a degradable core which contains a biologically active component, the core being surrounded by a plurality of outer segments such that the outer segments together form a liquid impermeable casing surrounding the core except at one or both ends of the bolus, whereby in use, the core can degrade from one or both ends as appropriate of the bolus to release the biologically active material and the outer segments are successively shed from the bolus.

In some forms of the bolus as defined in the preceding paragraph, the core may be surrounded by one or more subsidiary annular segments; for example of magnesium alloy, these in turn being surrounded by the outer segments which form the casing.

In some embodiments, each of the inner segments contains a biologically active component, each said inner segment preferably containing the same biologically active component. It will be appreciated that in all of the above described forms of the invention, instead of a single biologically active component, an inner segment may contain a combination of biologically active components. In some embodiments there are two types of inner segment, each type respectively containing a different biologically active material or a different combination of biologically active materials.

In one preferred form, the or each inner segment is generally cylindrical or disc shaped and when there is more than one, they may be held together by an interference fit between an annular protrusion on each disc and a recess on the next adjacent disc. Alternatively, the discs may be held in annuli which form the outer segments, the bolus being held together by interlocking between said outer segments as further described hereinbelow. In some embodiments, the or each inner segment is provided with a central hole or aperture through which extends a central rod, and the bolus may be held together at least partly by there being an interference fit between the segments and rod, the rod optionally being appropriately tapered or having a stepped diameter to assist co-operation therebetween. An adhesive or other locking compound may also be used to assist retention of the inner segments on the rod. Alternatively, as described above, flange members may extend inwardly from the outer segments and these flange members may locate in circumferential grooves around the rod, thereby holding the bolus together. The rod may be either of an inert or of a degradable material as desired. A preferred degradable material for this use is magnesium alloy. Such a rod may also be threaded, for example in the form of studding or of a bolt, and may be screwed through one or more other components of the bolus such as one or more of the inner segments. The rod need not be threaded along its entire length but only at positions corresponding to threading on another part or parts of the bolus.

The outer segments may be associated with and be attached to individual or pairs of the inner segments. The arrangement may then be such that the outer segments abut one another and create a seal therebetween. This seal may be formed by virtue of the natural texture and resilience of the material from which the outer segments are made, for example of a resilient plastics material such as polyvinyl chloride, or of a natural or a synthetic rubber such as a silicone, isoprene, styrene, butadiene, EPM, butyl, chloroprene, nitrile, polysulphide, polyurethane, chlorosulphonyl polyethylene, fluoro, acrylic, epichlorohydrin, polypropylene or a norbornene rubber. In this case the seal may be aided by deformation of the outer segment material, brought about by pressure between adjacent outer segments. Alternatively, there may be provided an annular sealing member between adjacent outer segments, for example an O-ring preferably of natural rubber, plastics or synthetic rubber such as silicone rubber.

In addition to, or in place of the O-ring, a suitable sealant material may be provided between the adjacent outer segments, this sealant being, for example, a grease or an adhesive. The use of O-rings and/or a sealant material between the adjacent outer segments is particularly desirable when the outer segments are made from a plastics material such as a thermoplastic, for example a styrene based, PVC, polyolefine, amorphous or crystalline thermoplastic or a thermosetting plastic. Examples of particular plastics materials for this use include acetal copolymer, acrylic, ABS, EVA, PTFE, methylpentene polymer, nylon 6.6, nylon 6, nylon 6.10, glass filled nylon, polycarbonate, polythethylene (high density or low density), polyethylene terephthalate, PPO, polypropylene, polystyrene (general purpose), polysulphone and unplasticised PVC. In some applications, the choice of plastics material may be restricted according to the intended use but will readily be determined by those skilled in the art. Such plastics material may thus be selected from any of those listed above or from plastics listed in Kempes Engineers Yearbook 1983, Morgan Grampion. In some embodiments the outer segments may comprise flat annular elastomeric or resilient plastics members which overlap one another in order to form the requisite seal.

The outer segments may be held adjacent to one another by virtue of being attached to one or more of the inner segments which are themselves held together as described above, or by means of the locking of inwardly extending flange members with a central rod, also as described above. Alternatively the outer segments may possess snap-fit projections and recesses to interlock with one another, or have projections which locate in grooves formed in adjacent inner segments, the outer segments then being so fashioned as to overlap one another in order to hold the bolus together. When the associated inner segment or segments have been degraded, the corresponding outer segment then becomes free of the bolus. If the bolus is located in the reticulo-rumenal sac of a ruminant, the thus freed outer segment is then excreted or, being of insufficient density to be retained, is simply regurgitated.

Particularly, though not exclusively, for administration to ruminant animals, in a further aspect the present invention provides a bolus comprising a plurality of axially spaced parts of a material which does not corrode in the rumeno-reticular sac and defining cavities or recesses therebetween, a biologically active substance in each said cavity or recess and means formed from a material which does corrode in the rumeno-reticular sac supporting the parts in such a manner that one end of said means is exposed, whereby when in use as the said means is corroded away the parts are successively shed from the assembly thereof each to release a dose of the biologically active material.

When intended as an intra rumenal device, regurgitation of any bolus according to the present invention may be prevented either by having a suitable geometric configuration, for example by being equipped with wings as described in U.K. Patent Specification No. 1 603 970, or by appropriate weighting. To ensure retention, it is generally necessary for the bolus to have a total density in the range of from 2.25 to 3.5 g/ml, preferably about 2.5 g/ml and, preferably, this density should increase as the bolus is progressively degraded. Whilst it is possible for the necessary weight to be provided simply by the materials from which the bolus is made, this can result in regurgitation of the device after a certain amount of it has been degraded in the rumen, as a result of its density having been reduced to below the minimum necessary to ensure its retention. Therefore, it is preferable that the bolus be provided with an additional weight.

The weight may be made from any suitable material or combination of materials sufficient to achieve the overall required bolus density. For example the weight may be fabricated from a generally inert material such as iron, steel, copper, tin, lead, tungsten, zinc, chromium, cobalt, nickel or manganese, or an alloy of two or more of such metals together or an alloy of one or more of such metals with one or more other metals. Particularly preferred is steel or iron or a zinc diecasting alloy. A weight of such inert metal would probably remain in the reticulo-rumenal sac after the rest of the bolus has degraded. Alternatively, a generally degradable material may be used, for example a degradable zinc alloy. The weight may, if desired, comprise a matrix of materials, for example shot of iron or other metal, dispersed in an inert (e.g. polymer) or degradable (e.g. magnesium alloy) base material. Where the base material is inert, the weight will generally be retained in the rumenal sac whereas when the base material is degradable, after it has been degraded, the shot may be sufficiently small to be excreted.

Yet again, the weight may simply comprise a suitably dense granular material, such as shot, held in a retaining sleeve, for example of a plastics material, or in a degradable shell, e.g. of magnesium alloy which itself is surrounded by a plastics or other inert sleeve. The granular material may be dispersed within the core of the device. Generally, the weight (of whatever form) may be provided at one end of the bolus or at any position along the length thereof, and/or as a central rod such as described above, in the latter case the rod then preferably being formed of an inert material.

A particular advantage is obtained when the weight is of a metal or metal alloy and is in contact with a central rod or degradable core (whether or not the core comprises a plurality of inner segments), which rod or core, at least in part, comprises a metal or metal alloy different from that of the weight. Then, when the weight and the rod or core both contact the liquid environment and the liquid environment is capable of acting as an electrolyte, a galvanic effect will arise. This will generally be the case when the bolus is in use in an animal's rumenoreticular sac or in impure water such as in a river or lake. The galvanic effect will regulate the rate of corrosion of the rod or core. When appropriate, to enhance the galvanic effect, the weight may be plated with a suitable metal different therefrom, or the weight may be provided with an insert of a suitable different metal or metal alloy.

For intra-rumenal use, a bolus according to the present invention will have weight and dimensions according to the particular ruminant animal for which it is intended. The particular weights and dimensions required in any given application will be apparent to those skilled in the art (for example having regard to the density requirements indicated above), but by way of example, a bolus for administration to cattle might have a length of from 30 to 200 mm, for example 50 to 150 mm, typically about 90 mm, a diameter of from 15 to 40 mm, for example 20 to 30 mm, typically about 25 mm, and in use deliver 2 to 10 doses, typically 5 doses of biologically active component(s) over a 1 to 12 month, for example 3 to 6 month, typically about 3½ month period, each dose comprising from 10 mg to 10 g, for example 100 mg to 1 g typically about 750 mg. The dependence of degradation of bovine intrarumenal boluses upon density and location in the reticulorumenal sac is described in J. L. Riner et al, Am. J. Vet-Res., 43, 2028–30. In normal use, it is convenient to administer the bolus to a ruminant by means of an oesophageal balling gun.

The biologically active component(s) of at least some of the inner segments is or are selected to have a desired effect in the environment in which the bolus is to be placed during use.

Where the bolus is designed for in vivo applications, i.e. to be located in humans or animals, the biologically active ingredients may be selected from therapeutic agents, vaccine formulations, nutrients and other substances necessary for the physical well being of the human or animal organism. Where the bolus is intended specifically for use in livestock, such a biologically active component may also be a growth promotant.

When the bolus is intended specifically for use in female humans, such a biologically active component may be an agent affecting fertility, for example a contraceptive or abortifacient agent.

Examples of therapeutic agents for in vivo use include anti-infectives, e.g., an antiviral agent such as acyclovir, idoxviridine or vidarabine; anti-bacterial agents such as penicillins, tetracyclines, erythromycin, neomycin, polymyxin B, gentamicin, nystatin, trimethoprim, cotrimoxazole or bacitracin; anti-protozoals such as amoebicides, for example emetine; anti-malarials, for example pyrimethamine or chloroquine; anti-coccidials, for example trimethoprim, trimethoprim in conjunction with sulphaquinoxaline (Trade Name: Tribrissen), Lasalocid (Trade Name), i.e. 3-methyl-6-[7-ethyl-4-hydroxy-3,5-dimethyl-6-oxo-7-[5-ethyl-3-methyl-5-(5-ethyl-5-hydroxy-6-methyl-2-tetrahydropyranyl)-2-tetrahydrofuryl]heptyl]-salicyclic acid or the compound described in U.K. Patent Specification No. 2 027 013B (otherwise designated M 139603 and believed to have the chemical structure of 2,3,4,5-tetrahydro-3-[(2S)-2-{(1S,2R,6S)-6-[(E)-2-}(2R,3R,6S)-3,4,5,6-tetrahydro-6-[(3S,E)-3-{(2R,3S,5R)-2,3,4,5-tetrahydro-5-[(1S-)-1-methoxyethyl]-3-methylfur-2-yl}-but-1-enyl]-3-methyl-2H-pyran-2-yl{-3-hyroxyprop-1-enyl]-2-methylcyclohexyl}propionyl]furan-2,4-dione, sodium salt); anti-theilerials, for example parvaquone; anti-trichomonals, for example metronidazole; and anti-leishmanials, for example sodium stibogluconate. Other suitable anti-infectives include anti-fungal agents (including agents having activity against yeast and yeast-like organisms (e.g. Candida) and against dermatophytes). An example of such an antifungal agent is nystatin.

Therapeutic agents for use in the bolus of the present invention also include anti-parasitic agents such as anthelmintics, for example oxfendazole (i.e. 2-methoxycarbonylamino-5-phenylsulphinylbenzimidazole), oxibendazole, parbendazole, niridazole, mebendazole, fenbendazole, cambendazole, albendazole, metronidazole, thiabendazole, levamisole, tetramisole, closantel, bromoxanide, rafoxanide, clioxanide, oxyclozanide, salantel, morantel, resorantel, pyrantel, praziquantel, febantel, oxantel, carbantel, piperazine, niclosamide, brotianide, thiophanate, bephenium, pyrvinium, diethylcarbamazine, suramin, dichlorophen, paromomycin, stibophen, antimony sodium dimercaptosuccinate, hycanthone, metrifonate, antimony barium tartrate, antimony potassium tartrate, chloroquine, emethine, bithionol, hexylresorcinol, tetrachloroethylene, mirasan, miracil, lucanthone, furapromidium, oxamniquine, tuhecidin, amphotalide, nicarbazin, Hetol (Trade Name), Hetolin (Trade Name), nitroxynil, disophenol, Bitin-S (Trade Name), bromofenophos, menichlopolan, thiosalicylanilide, diamphenethide, bunamidine, bitoscanate, nitroscanate, amoscanate, diuredosan, arsenamide, thiazothienol, thiazothielite, haloxon, dithiazanide iodide, bidimazium iodide, methyridine dymanthine trichlabendazole, chlorsulan and avermectins. Also suitable are agents for countering maggot fly, screw-worm, ticks and mange, e.g., pyrethroids such as permethrin, deltamethrin, cypermethrin, flumethrin or fenvalerate, and also parasitic repellants. In particular the latter agents include those which are administered to animals and have insecticidal or tickicidal effects after excretion in the faeces.

Other suitable therapeutic agents, particularly for administration to humans, include cardioactive compounds such as cardiotonic agents, anti-arrhythmics, anti-thrombotics, and agents having a general hypotensive effect on the cardiovascular system. Included in this group are those of the natural prostaglandins exhibiting cardiovascular effects (e.g. epoprostenol) as well as agents which are mimetics, agonists or antagonists of such prostaglandins.

Therapeutic agents, for use in the bolus of the present invention, also include compounds having anti-tumour (e.g. cytotoxic), anti-depressant, anti-convulsant, anorectic, analgesic, antipyretic and anti-inflammatory (including anti-ulcer) activity. Included in the latter group are the corticosteroids such as hydrocortisone, as well as non-steroidal agents such as anti-inflammatory pyrazolines. A further group of suitable therapeutic agents includes those having an effect on the upper and/or lower respiratory tract, including anti-histamines, anti-tussives and anti-asthmatics (including bronchodilators).

Nutrients or other substances conducive to physical health, for use in the bolus according to the present invention, include vitamins and agents which have a vitamin-like physiological role. Vitamin mixes, particularly containing one or more B vitamins, may be included for the treatment of fodder poisoning or acute bacterial toxaemia in animals. For the assistance of re-hydration in fluid-electrolyte loss associated with scours in calves, lambs and pigs, the biologically active material in the bolus of the invention may comprise a composition of suitable electrolytes including sodium chloride, and/or one or more appropriate sugars, for example glucose. Particularly when intended for administration to grazing animals, such nutrients may include trace elements, for example selected from magnesium, zinc, copper, cobalt and selenium.

When insecticidal or like properties are required, for instance when the bolus is intended for use in rivers, lakes, ponds, pools and like liquid environments, the active agent in the bolus of the invention may include a release agent which releases appropriate ions into the liquid. For instance, the release agent may comprise a soluble glass which will deliver, into an aqueous environment, copper ions which will kill schistosme-carrying snails, or will deliver silver ions to kill bacteria such as *Vibrio cholerae*, the organism which causes cholera. In the case where the active agent is required to kill or control other insects or parasites, such agent will consist of or include an appropriate insecticide or parasiticide which is correspondingly released as the bolus is eroded. Thus, in the case where malarial mosquito-infected water is to be treated, the active ingredient in the bolus will be, for instance, a pyrethroid, such as permethrin, deltamethrin, flumethrin or fenvalerate.

Particularly preferred are boluses wherein either the central rod (when present) and/or at least some of the inner segments are of a degradable metal such as aluminium, zinc, titanium and their alloys, or especially an alloy of magnesium and one or more other metals, for example selected from the following (all percentages being by weight): silicon up to 1.5%, nickel up to 1%, zinc up to 15% (for example about 12%), manganese up to 2%, copper up to 4% (for example about 2% or about 3%), aluminium up to 15% (for example about 12%), and zirconium up to 0.8%. Cobalt and/or selenium may also be present in trace quantities. It will be appreciated by those skilled in the art that not all of the above metals are mutually compatible. For example, it is not generally possible to include both aluminium and zirconium together in the alloy and manganese is incompatible with copper and aluminium so that, for example, when aluminium is present in the alloy it is not possible to have more than 0.6% of manganese present.

The anti-coccidial agents Lasalocid and M 139603, referred to above, are also growth promotants and may be used as a biologically active component when the bolus is for administration to livestock. Other suitable growth promotants include virginiamycin, zinc bacitracin, flavomycin, avoparcin, nitrovin, thiopeptin, halquinol, carbadox, tylosin and arsanilic acid (including carbarsone). Some of these agents (e.g. zinc bacitracin)

are also antibacterial agents. The following agents, commonly used as antibacterial feed additives for cattle, may also be used as one or more biologically active components in the bolus according to the invention, either for their anti-bacterial and/or growth promotant properties: bacitracin, bacitracin methylene disalicylate, chlortetracycline, chlortetracycline plus sulphamethazine, ethylenediamine dihydriodide, melengestrol acetate, monensin, monensin plus tylosin, neomycin base, oxytetracycline, sodium arsanilate, erythromycin, lincomycin, oleandomycin, penicillin and roxarsone.

In the case of administration to female humans, agents affecting fertility include oestradiol and compounds with a comparable pharmacological profile as well as appropriate prostaglandins such as $PFG_{2\alpha}$. For enhancing the fertility of animals or inducing ovulation, one or more appropriate hormone or hormone mimetics such as prostalene, optionally in combination with vitamin E, may be included.

Where the biologically active component is an appropriate metal intended as a trace element for animals as described above, this will generally possess natural rigidity and alone or as an alloy with another metal or metals can degrade in the rumenal fluids. Moreover, it is possible to formulate the metal so as to have one or more biologically active agents dispersed therein. However, for most other biologically active compounds alone or in combination, it will be necessary to formulate them as compressed powders, optionally with a binder, for example in tablet form.

In particular, therapeutic agents may be provided in discrete units such as capsules, cachets or tablets, each containing a predetermined amount of agent, as a powder or granules. Such formulations may be prepared by any of the methods of pharmacy and may include the step of bringing into association the agent with a binder and/or carrier which constitutes one or more accessory ingredients. In general they are prepared by uniformly and intimately admixing the agent with liquid or finely divided solid carriers or both, and then, if necessary, shaping the product into the desired presentation. For example, a tablet may be prepared by compression or moulding a powder or granules of the agent, optionally with one or more accessory ingredients. Compressed tablets may be prepared by compressing, in a suitable machine, the agent in a freeflowing form such as a powder or granules optionally mixed with a binder, lubricant, inert diluent, surface active or dispersing agent(s). Moulded tablets may be made by moulding, in a suitable machine, the powdered agent moistened with an inert liquid diluent. Alternatively, such formulation may be prepared by admixture of the agent with one or more of the conventional solid carriers, for example cocoa butter, and shaping of the resulting mixture.

When the therapeutic agent is formulated as a tablet, the tablet may have, for example, especially for administration to cattle, a weight in the range of 0.5 to 5 g, for example 0.75 to 2 g, typically about 1 g. The overall diameter of the tablet might be in the range of from 10 to 25 mm, typically about 15 to 19 mm. When the tablet is provided with a central hole through which extends the central rod, typically this may have a diameter in the range of from 4 to 15 mm, for example about 12.55 mm. The weight of active ingredient in the tablet may for example be in the range of from 50 to 95% w/w, typically about 75% w/w. Suitable binders, carriers and other diluents include disintegrants such as starch, e.g. 5 to 15%, typically 10% w/w, binders such as polyvinylpyrrolidene (PVP), e.g. 0.5 to 5% w/w, typically 2.5% w/w and lubricants such as magnesium stearate, e.g. 0.2 to 2.5% w/w, typically 1.0% w/w. In any tablet formulation, if desired, the remaining bulk of the tablet may be made up with a material such as lactose. It will be appreciated that such compositions may also be formulated as a cylinder when intended for use in a bolus having a single primary inner segment constituting a core. Such a cylinder may have a weight of e.g. 5 to 100 g, typically about 80 g, a diameter from 4 to 25 mm, typically about 17 mm and an overall length of e.g. 40 to 120 mm, typically about 100 mm.

For inner segments which do not contain any biologically active components, suitable degradable materials include waxes, soluble glasses, biodegradable polymers, compressed powders, plaster of Paris and the like. Such materials may also be used for inner segments which contain one or more biologically active components, said component(s) then being dispersed in the latter material.

The invention will be described further, by way of example, with reference to the accompanying drawings in which:

FIG. 6 is longitudinal section illustrating another embodiment of the bolus of the invention;

FIG. 7 is a cross section taken on the line VII—VII of FIG. 6;

FIGS. 8 to 13 are longitudinal sections illustrating six further embodiments of the bolus of the present invention in each of which the inner segments are supported on a central rod;

Figure 1:
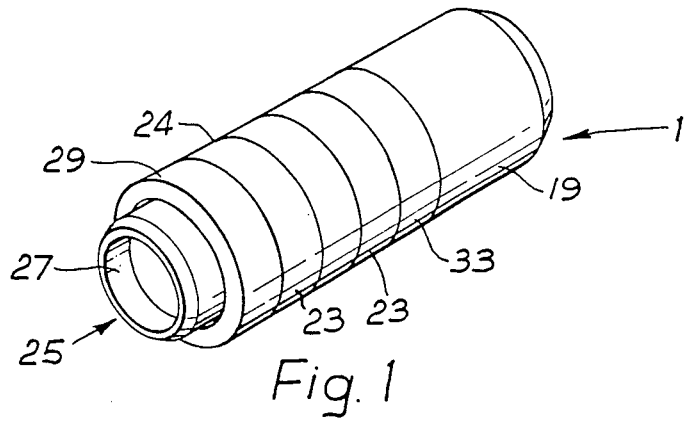
FIG. 1 is a perspective view illustrating a first embodiment of the bolus of the present invention.
Figure 2:
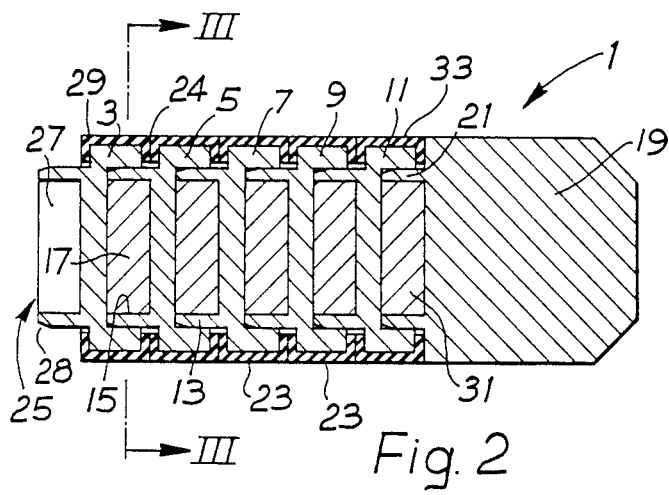
FIG. 2 is a longitudinal section through the bolus of FIG. 1.
Figure 3:
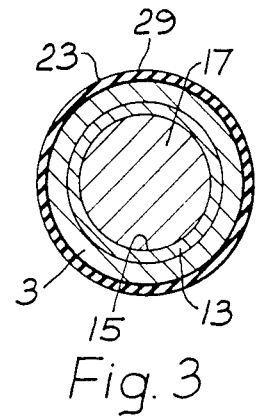
FIG. 3 is a cross section taken on the line III—III of FIG. 2.

FIGS. 1 to 4 of the drawings illustrate a first embodiment of the release device of the invention. This is in the form of an elongate cylindrical bolus 1 particularly suitable for use as an intrarumenal device. The bolus 1 comprises disc-shaped magnesium alloy inner segments 3, 5, 7, 9 and 11 which are held together by an annular protrusion 13 on each said segment being an interference fit into a complementary socket in the next adjacent segment, the annular protrusions 13 defining respective recesses 15. In the bolus according of FIGS. 1 to 4 and, unless indicated to the contrary, in any embodiment described hereinafter, the magnesium alloy is a magnesium alloy containing 12% aluminium and 2% copper, the percentages being by weight. Accommodated in each recess 15 is a respective tablet 17 containing a biologically active material in the form of an anthelmintic formulation, preferably of oxfendazole or levamisole. These tablets constitute inner segments of a second kind. The tablets 17 and the magnesium alloy segments 3, 5, 7, 9 and 11 constitute a core of the bolus 1. To ensure that in use the bolus is retained in the rumen, a steel endweight 19 is also provided. This is attached to the bolus 1 by means of an annular protrusion 21 comparable with the protrusions 13 in the magnesium alloy segments 3, 5, 7, 9, 11. Each magnesium alloy inner segment 3, 5, 7, 9, 11 is surrounded by a respective silicone rubber outer segment 23 of U-shaped radial section. The dimensions of these outer segments 23 are such that when the bolus 1 is assembled as shown, the outer segments 23 are compressed so that joints 24 therebetween are effectively sealed. Thus, the outer segments 23 together form a liquid impermeable casing of the bolus.

When the bolus 1 is administered to a ruminant animal, the magnesium alloy of the inner segment 3 at the uncovered end 25 of the bolus 1 begins to degrade, probably by corrosion and/or erosion. It will be noted that there is no anthelmintic tablet in recess 27 in magnesium alloy segment 3, although if desired, such a tablet could be included in this recess 17 to provide an initial dose of anthelmintic immediately upon administration of the bolus 1. This initial tablet may be retained by crimping the annular protrusion of the first segment 3, which protrusion is indicated by the reference numeral 28, by appropriate bending of the edge of the protrusion 28, or by capping the recess 27, for example with a suitable magnesium alloy cap (not shown). Alternatively, such an initial tablet may be retained by means of a suitable adhesive. However when, as shown, there is no tablet in first recess 27, after the degradation has progressed sufficiently, the first tablet 17 is exposed, thus administering a first dose of anthelmintic to the animal. When, substantially all of the disc of the segment 3 has degraded, there will no longer be sufficient support for the endmost outer segment which is indicated by the reference numeral 29 and which then falls away and eventually either is excreted or, because it is of insufficient weight, is regurgitated.

Degradation of the magnesium alloy segments 3, 5, 7, 9 and 11 proceeds progressively, with doses of anthelmintic being administered to the animal at regular intervals. When the last tablet, which is indicated by the reference numeral 31, has been administered and the last silicone rubber outer segment 33 has fallen away, only the end weight 19 remains. This stays in the rumen or is excreted, depending on its dimensions and weight. It will be appreciated that the degradation of the magnesium alloy segments serves not only to administer regular anthelmintic doses but also to supply the nutritional trace element magnesium to the animal.

Figure 4A:
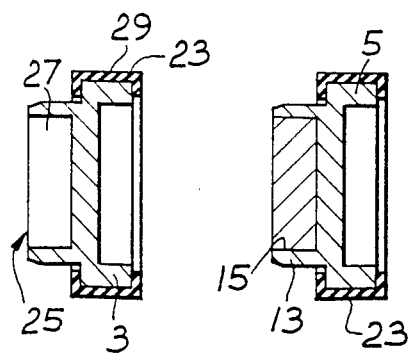
FIGS. 4A and 4B are sectional views showing the first two outer segments (and associated inner segments) of the bolus of FIGS. 1 to 3, prior to assembly.
Figure 4B:
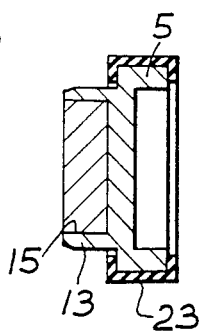

FIG. 4 shows in detail the first two magnesium alloy segments 3 and 5 prior to assembly, together with the anthelmintic tablet in the recess 15 of the segment 5 and the respective silicone rubber outer segments 23.

Figures 5A, 5B:
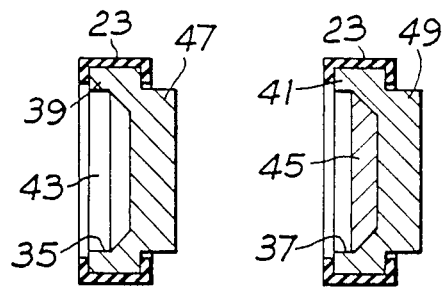
FIGS. 5A and 5B are views similar to FIGS. 4A and 4B but showing an alternative form for the segments.

FIG. 5 shows an alternative construction for the magnesium alloy segments. Here, respective recesses 35, 37 are provided in the discs of the magnesium alloy segments 39, 41 themselves, instead of being defined by annular protrusions 21 as in the embodiment of FIGS. 1 to 4. As in the previous embodiment, the recess 35, indicated by the reference numeral 43, in the front segment 39 is empty, but anthelmintic tablets 45 are provided in the subsequent segments 41. The segments 39, 41 are formed with respective raised circular protrusions 47, 49 for locating in the complementary recesses 37 in the adjacent segments. Silicone rubber outer segments 23 are provided as for the bolus of FIGS. 1 to 4 and form seals in the same way when the bolus is assembled.

FIGS. 6 and 7 depict a further embodiment of the release device of the present invention in the form of a bolus 50 comprising a series of disc-shaped magnesium alloy inner segments 51 which are interconnected by an integral longitudinal magnesium alloy spine 53. The magnesium alloy inner segments 51 alternate with inner segments 55 each of an anthelmintic composition. Surrounding the inner segments 51 and 55 are outer segments 57 of an elastomeric or resilient or non-resilient plastics material. The outer segments 57 fit tightly over the exteriors of the inner segments 51 and 55 and overlap so as to form a liquid impermeable sleeve. These outer segments 57 may alternatively be of a heat shrinkable polymer, shrunk onto the inner segments 51 and 55. Also provided is a steel end-weight 59 to ensure retention, this weight 59 being fixedly attached in direct contact with one of the segments 51 by an endmost one of the outer segments 57. It will be appreciated that in use, this bolus functions in an analogous manner to that described above with reference to FIGS. 1 to 4.

Bolus 61 shown in FIG. 8 comprises disc-shaped magnesium alloy inner segments 62 which each have a central threaded hole 63 and are screwed over a shank 65 of nylon studding having a complementary thread 69. Each magnesium alloy inner segment 62 is surrounded by a respective silicone rubber outer segment 71. The magnesium alloy inner segments 62 are formed with respective recesses 73 which contain respective tablets 75 of an anthelmintic composition. The tablets 75 have central holes 77 of such dimensions that they fit loosely over the thread 69 of the nylon studding shank 65. End weight 79 is also appropriately threaded and screwed onto the shank 65. The magnesium alloy inner segments 62 are screwed on sufficiently tightly so that the silicone rubber outer segments 71 are compressed together as at 81, and collectively form a liquid impermeable casing of the bolus 61.

Bolus 84 shown in FIG. 9 is constructed in a form similar to the bolus 61 of FIG. 8, but with the difference that shank 85 is of magnesium alloy. Magnesium alloy inner segments 89 are provided with respective threaded central holes 91 through which the shank 85 is screwed. A threaded cavity 93 is provided in end weight 95 for the latter to screw onto the shank 85. As with the bolus of FIG. 8, the magnesium alloy inner segments 89 are screwed onto the shank 85 so that silicone rubber outer segments 97 seal together to form a liquid impermeable casing of the bolus. Anthelmintic tablets constituting the tablets inner segments 99 are of the same form as the tablets 75 of the bolus 61 of FIG. 8. The rate of disintegration of the bolus 84 of FIG. 9 is primarily determined by the degradation of the magnesium alloy shank 85, whereas for the bolus of FIG. 8, this rate depends mainly on the degradation of the magnesium alloy inner segments 62.

A further variant of the release device of the invention is indicated at 101 in FIG. 10. In this device, magnesium alloy bar 103 is an interference fit in holes 105 in moulded plastics outer segments 107 having respective inwardly extending flanges 109 which also act as spacers between respective anthelmintic tablet inner segments 111 having respective central holes 113 which fit loosely over the bar 103 which is also secured by being an interference fit in a hole 115 in an end weight 117. If the plastics outer segments 107 and the end weight 117 fit to the bar 103 sufficiently tightly, the outer joints between the adjacent outer segments 107 will seal and prevent ingress of liquid.

Alternatively, it is apparent that in this embodiment, the components of the bolus 101 may be retained on a central rod 103 equivalent to the bar, by means of an interco-operating thread arrangement, e.g. if the central rod is in the form of studding, although this may not necessarily be threaded along its entire length. Corresponding threads will then be provided in the holes 105 and the hole 115. However, it will be appreciated that if the studding is provided with a head and arranged to emerge from the end weight 117 at the end of the latter remote from the segments 107 and 111 i.e. as a bolt, then it is not necessary for the hole 115 in the end weight 117 to be threaded. Similarly in the embodiments of FIGS. 8 and 9, if the shank 65 or 85 is provided with a head where it emerges at one end of the bolus, then it is not necessary to thread the holes in the centres of the magnesium alloy inner segments 62, 89. In the latter two cases (FIGS. 8 and 9), instead of providing a head on the shank 65 or 85 so that it is a bolt, it is possible just to thread the hole 91 through the endmost magnesium alloy inner segment 62 or 89.

Figure 11:
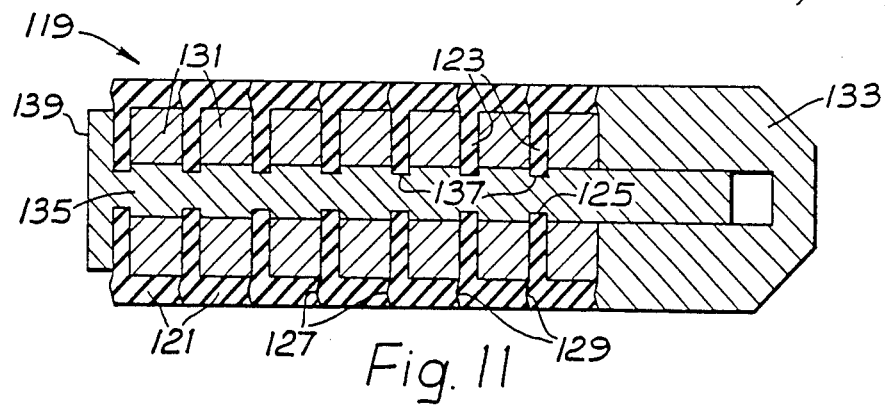

Referring now to FIG. 11, bolus 119 in this embodiment comprises a plurality of plastics outer segments 121, each having a respective inwardly extending flange 123 formed with a central aperture 125. Each such outer segment 121 has a respective axially facing peripheral annular ridge 127 and a complementary axially facing peripheral annular groove 129 the cross-section of which is adapted to receive the peripheral ridge 127 of the adjacent segment 121 so that the segments 121 can be stacked together as shown in nested relationship to define a plurality of cavities each containing a respective filling 131 of biologically active material. The stack is completed by an end weight 133. The flanges 123 are located on a substantially cylindrical rod 135, one end of which is embedded in the end weight 133. The rod 135 extends through the apertures 125 in the flanges 123 and is formed with axially spaced circumferential grooves 137 into which the flanges 123 locate. The spacing between the grooves 137 is such, having regard to any resilience of the flanges 123, that the confronting peripheral ridges 127 and grooves 129 are urged together to form liquid tight joints.

When this bolus is in use, a disc 139 on the end of the rod 135 remote from the end weight 133 is exposed to the interior of the rumeno-reticular sac of an animal. Each of the fillings 131 consists of or contains an anthelmintic composition which may be in tablet, powdered, paste or other form. The animal's rumen juices degrade the rod 135 axially, over a period of time, typically several weeks or even months, thus to shed the outer segments 121 successively and hence to release the fillings 131 as succesive doses of the biologically active material, at timed intervals. The time taken for each dose to be released is determined by the spacing between the flanges 123 and by the composition of the rod 135. After the last segment 121 has been shed, the rumen juices will eventually degrade the end weight 133 which is of an appropriate zinc alloy. The segments 121 are, of course, successively freed to be discharged by excretion or regurgitation.

Figure 12:
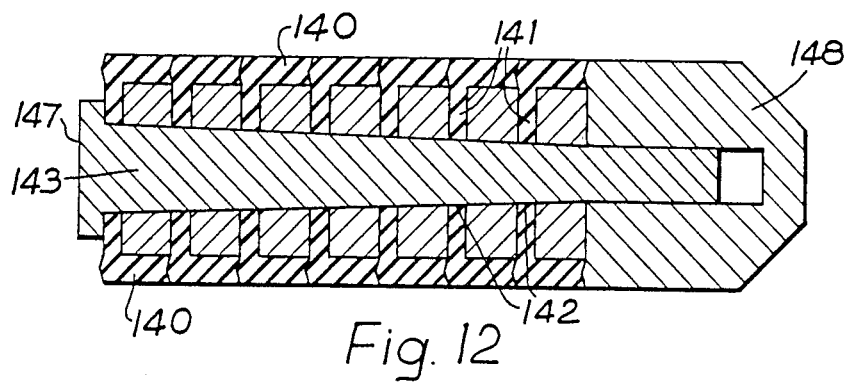
Figure 13:
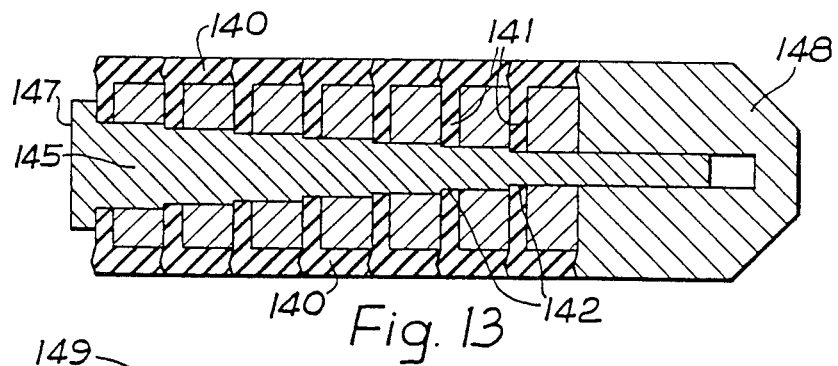

FIGS. 12 and 13 show variations of the bolus of FIG. 11. In these embodiments, flanges 141 of outer segments 140 have apertures 142 of different diameters and are located on a tapered rod 143 (FIG. 12) or a stepped rod 145 (FIG. 13). The seals between the outer segments 140 may be aided by pressure on the outer segments 140 and their associated flanges 141 exerted between bolt head 147 and end weight 148 by reason of the latter being screwed onto the rod 143, and/or the effect of an interference fit between the flanges 141 and the rod 143 or 145.

Figure 14:
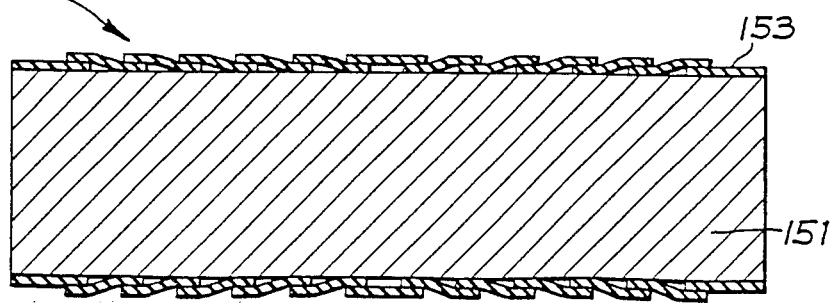
FIG. 14 is longitudinal section illustrating another embodiment of the bolus according to the invention, this having a single inner segment comprising the core.

FIG. 14 shows a bolus 149 having a core comprising a single inner segment 151, comprising a matrix of a material such as a wax, an erodible or biodegradable polymer, a bulk of compressed metallic particles, or plaster of Paris. A therapeutic agent, such as an anthelmintic, is dispersed within the matrix which is surrounded by a plurality of outer segments 153 having the same construction and fitment as those of the embodiment shown in FIGS. 6 and 7. This particular bolus provides continuous, rather than pulsed, release of the therapeutic agent. Since in the device, as shown, there is no end weight, after the majority of the device has degraded, the remnant is regurgitated or excreted. However, to ensure retention until all of the agent has been released, it is possible to provide an additional weight (not shown), e.g. as a central rod, or a weight of appropriate construction disposed at an end or along the length of the bolus.

Figure 15:
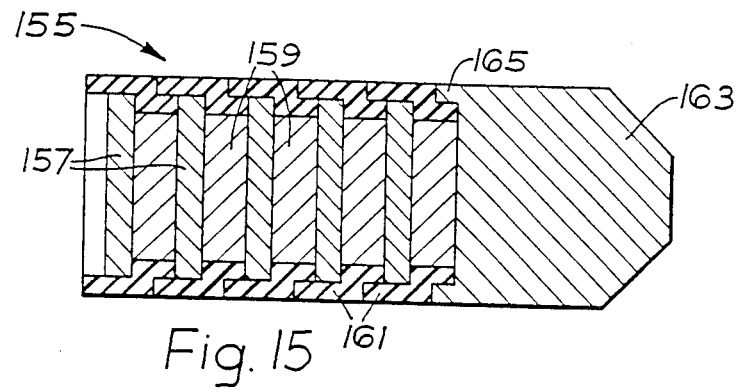
FIG. 15 is a longitudinal section illustrating yet a further embodiment of the bolus of the invention.

Another form of intra-rumenal bolus 155 which is primarily suitable for pulsed release is shown in FIG. 15. A core of the bolus comprises alternately-arranged magnesium alloy inner segments 157 and anthelmintic tablet inner segments 159 which are held together by overlapping resilient outer segments 161 of a plastics or elastomeric material which together form a liquid impermeable casing or sleeve. A steel end weight 163 locates onto an endmost outer segment 161 by means of a peripheral lip 165.

Figure 16:
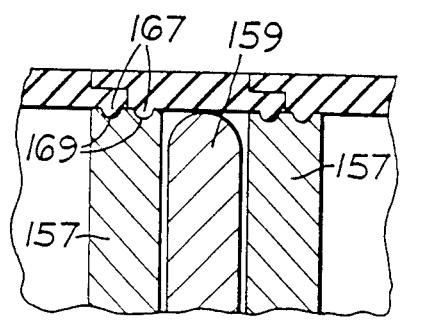
FIG. 16 is an enlarged fragmentary sectional view illustrating an alternative interlocking arrangement for the inner and outer segments of the bolus of FIG. 15.

Inter-locking between the magnesium alloy inner segments 157 and outer segments 161 can be improved as shown in FIG. 16. Here, circumferential ridges 167 on the inner surfaces of the outer segments 161 locate in corresponding circumferential grooves 169 in the magnesium alloy inner segments 157, thus inhibiting relative movement. The anthelmintic tablet segments 159 are sandwiched between the magnesium alloy inner segments 157 as described above.

In each of the embodiments described above, the seals between the adjacent outer segments, so that they form a liquid impermeable sleeve, is effected by compression therebetween, and relies on the properties of the materials from which the outer segments are fabricated. However, it is also possible to utilise other inert materials which would not necessarily form a suitable seal when compressed together. Sealing may then be advantageously achieved by rubber or synthetic rubber O-ring seals between adjacent outer segments as shown in FIGS. 17 to 20. In all of these embodiments, the segments are held together by a respective snap-lock arrangement which also serves to compress the O-ring to effect the requisite seal.

Figure 17:
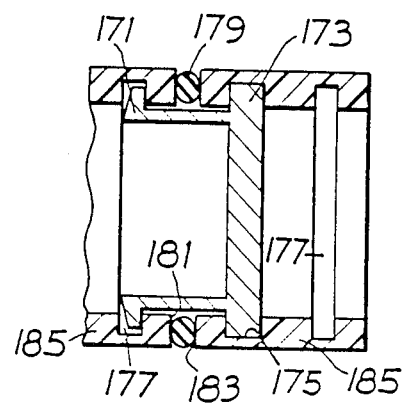
FIGS. 17 to 20 are enlarged fragmentary sectional views illustrating four alternative arrangements wherein there are O-ring seals between adjacent outer segments which fit together by snap-lock means.

In FIG. 17, snap lock components 171 are integral with magnesuim alloy inner segments 173 located in respective grooves 175. The snap lock components 171 lock into respective grooves 177. A respective O-ring 179 is compressed between the confronting flat surfaces 18 and 183 of adjacent plastics outer segments 185.

Figure 18:
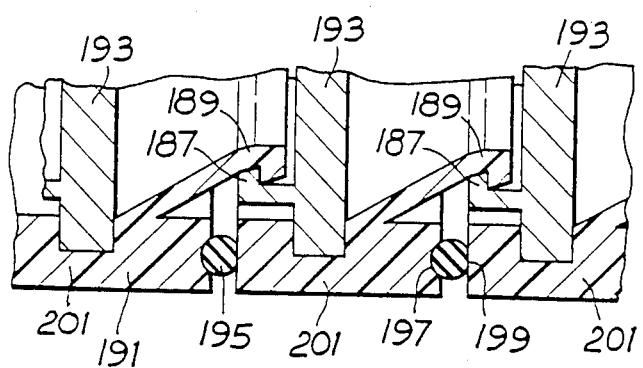

In FIG. 18, snap lock component 187 locates under a respective corresponding lug 189. Again, each snap lock component 187 is integral with a respective magnesium alloy inner segment 193. A respective O-ring 195 is located in a groove 197 in each outer segment 201 and is compressed against flat surface 199 on the adjacent outer segment 201.

Figure 19:
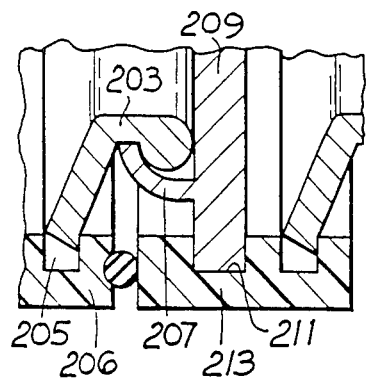

In FIG. 19 the arrangement is similar to that shown in FIG. 18, but differs therefrom in that a separate snap-in moulding 203 locates in a respective groove 205 in each outer segment 206 and locks over a lug 207 integral with a magnesium alloy inner segment 209 which is held in a respective slot 211 in the adjacent outer segment which is indicated by the reference numeral 213.

Figure 20:
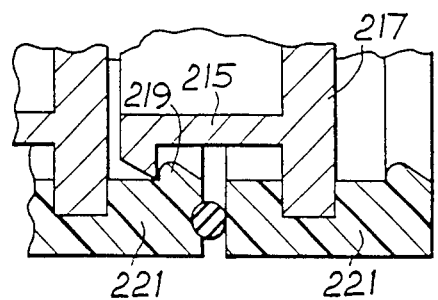

The embodiment of FIG. 20 is comparable with those depicted in FIGS. 18 and 19, but with the difference that a respective thin section 215 of magnesium alloy, integral with each magnesium alloy inner segment 217, locks over a projection 219 on the next adjacent plastics outer segment 221.

Figure 21:
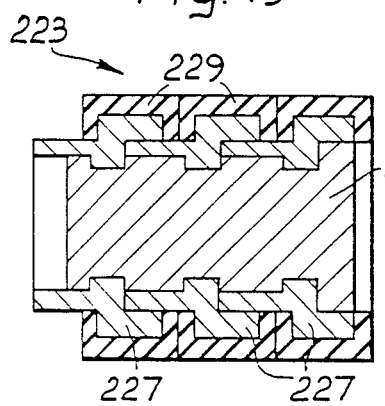
FIG. 21 is a longitudinal section illustrating another embodiment of the bolus, which is comparable with that shown in FIG. 14.

FIG. 21 shows another embodiment of the bolus of the invention in which there is a core in the form of a single segment comparable with that of FIG. 14. This bolus 223 has a core comprising an inner segment 225 of biologically-active material corresponding to that of the device in FIG. 14. Subsidiary interlocking inner segments 227 are of magnesium alloy and are surrounded by silicone rubber outer segments 229. In use, as the inner segment 225 is degraded, the outermost magnesium alloy inner segments is also degraded, progressively undermining their support for the outer segments 229 which are thus successively shed. As with the device of FIG. 14, an additional weight (not shown) may be provided. This may, for example, be a central rod or an end weight such as has been described above, or in the alternative, as is described below with reference to FIG. 22. Although only three magnesium alloy inner segments 227 (with corresponding outer segments 229) are shown, the device may be made in any appropriate length, for example having up to ten or more magnesium alloy inner segments 227.

Figure 22:
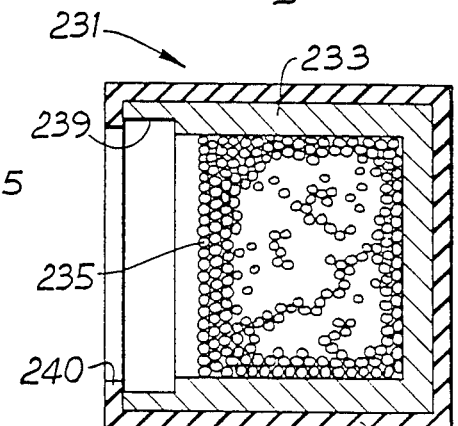
FIG. 22 is a longitudinal section through an end weight which may be used as an alternative to the weights illustrated in connection with the various illustrated embodiments of the bolus.

In FIG. 22 there is shown an alternative form of end weight 231 which may be used in conjunction with any of the embodiments of the bolus as herein described. This end weight 231 comprises a magnesium alloy shell 233 which holds iron shot 235. The shell 233 is surrounded by an injection moulded plastics or synthetic rubber sheath 237. Recess 239 in the shell 233 enables the shell 233 to be fitted to the endmost outer segment of its bolus in a manner similar to the end weight 163 in the embodiment of FIG. 15, the corresponding end of the shell 233 being overhung by a lip 240 which ensures that the weight is a tight interference fit to the endmost segment. It will be readily apparent that such an arrangement may be adapted to attach the weight to any other embodiment of the bolus according to the invention. It will be appreciated that if such a weight is provided at a position along the length of the bolus, then the sheath needs only to surround the shell circumferentially, so that the shot is exposed at both ends of the weight, prior to its incorporation in the bolus. Such a weight may be used, for example, in the device described below with reference to FIG. 23.

Figure 23:
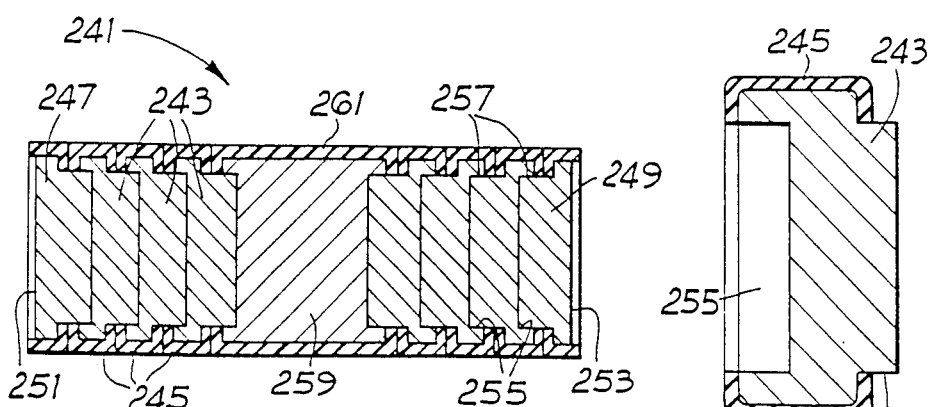
FIG. 23 is a longitudinal section illustrating another embodiment of the bolus according to the invention, which is particularly suitable for the control of hypomagnesaemia.
Figure 24:
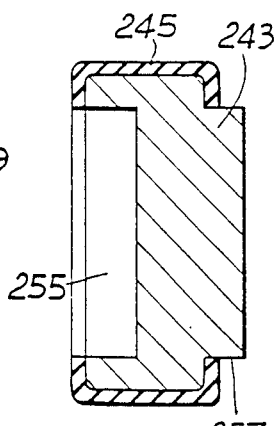
FIG. 24 is a sectional elevation illustrating one of the inner segments of the bolus shown in FIG. 23.

FIG. 23 shows a form of bolus 241 according to the present invention which is particularly suitable for the treatment of hypomagnesaemia (magnesium deficiency) in grazing ruminants. In this bolus 241, interlocking magnesium alloy inner segments 243 are surrounded by silicone rubber outer segments 245 which together form a liquid impermeable casing. One of the inner segments 243 with its associated outer segment 245 is depicted in FIG. 24. In the bolus 241 the two end inner segments 247 and 249 present respective substantially flat outer surfaces 251, 253 in contrast to the other inner segments 243 which have respective recesses 255 and opposed circular projections 257 to permit interlocking. To prevent regurgitation, a weighted slug 259 is provided mid-way along the length of the bolus 241. This slug 259 has a circumferential sheath 261 which constitutes a further outer segment forming part of the outer liquid impermeable casing of the bolus 241.

Figure 25:
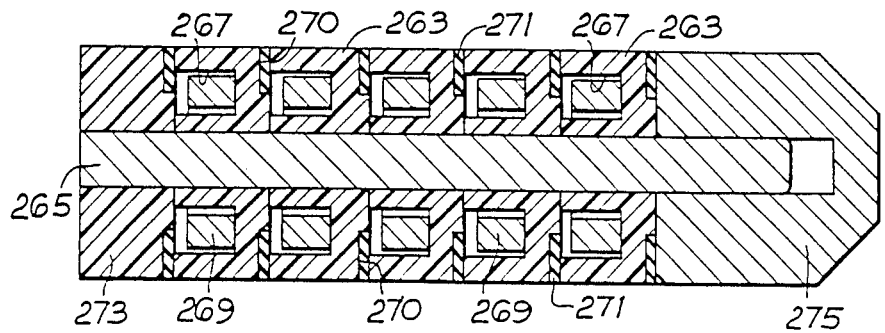
FIG. 25 is a longitudinal section illustrating yet another preferred embodiment of the bolus of the invention.

FIG. 25 illustrates a particularly preferred embodiment of the bolus of the invention which comprises a plurality of disc-form outer segments 263, e.g. of polyvinyl chloride, which are a tight or interference fit on a central rod 265 of magnesium alloy. Each segment 263 is of a configuration providing an annular recess 267 opening to one side face thereof and loosely accommodating a respective inner segment 269 in the form of an annulus or ring of or containing a biologically active composition such as an anthelmintic, preferably oxfendazole or levamisole. The segments 269 and the rod 265 constitute respective inner core components of the bolus.

For sealing the recesses 266 against undesired ingress of liquid, each segment 263 has, around its flat face remote from that to which the recess 267 opens, a circumferential relief 270 defining a concentric shoulder upon which locates a respective sealing washer 271, of silicone rubber, against which the confronting flat face of the next adjacent segment 263 counterseals.

At one end, the central rod 265 has thereon a disc-form dummy segment or end cap 273, also of a liquid impermeable material such as polyvinyl chloride, through the entire depth of which the rod 265 extends so as to be exposed at the side remote from the outer segments 263. A respective sealing washer 271 provides a seal between this dummy segment 273 and the recess 267 of the adjacent outer segment 263.

At the other end, a steel end weight 275 comparable with the weights described with reference to the preceding embodiments, is provided on the rod 265.

It will be appreciated that with this embodiment (in which in an alternative configuration, the dummy segment 273, the outer segments 263, and end weight 275 may be threadedly engaged onto the rod 265) after administration, one obtains firstly a gradual and continuous erosion, corrosion or dissolution of the magnesium alloy rod 265, starting at the dummy segment end, and continuing constantly until the dummy segment 273, outer segments 263 and sealing washers 271 are discharged e.g. by regurgitation. Thus the inner segments 269 are successively released as pulsed doses. The end weight 275 will most probably be retained by virtue of its density but the small residue of the rod 265 within the end weight will eventually also corrode away.

In addition to gradual release of magnesium from the rod 265 into the rumen juices of the dosed animal, the inner segments 269 are released in succession so as to provide the plurality of pulsed doses of the therapeutic agent present in such segments 269. Obviously, the bolus may be constructed with any desired number of the outer segments 263 to provide a corresponding number of pulsed doses, and the release of the magnesium and the timing of the release of the pulsed doses may be controlled by appropriate selection of both the physical dimensions of, and the composition of, the rod 265.

Figure 26:
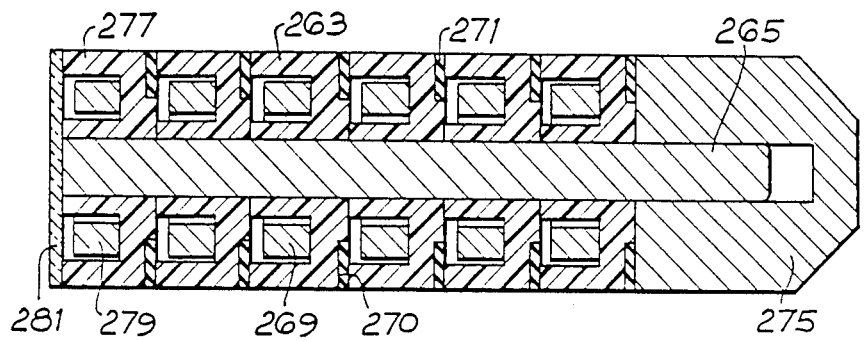
FIG. 26 is a view similar to FIG. 25, but showing a modification.

The bolus of FIG. 26 corresponds to that of FIG. 25 except that in the place of the dummy segment 273 there is an additional outer segment 277 containing an additional dose in the form of extra inner segment 279. This is masked by a degradable, e.g. wax blanking piece 281 which is readily eroded in the rumen to enable the first dose provided by the extra inner segment 279 to be released almost immediately, e.g. after only 1 or 2 days.

Figure 27:
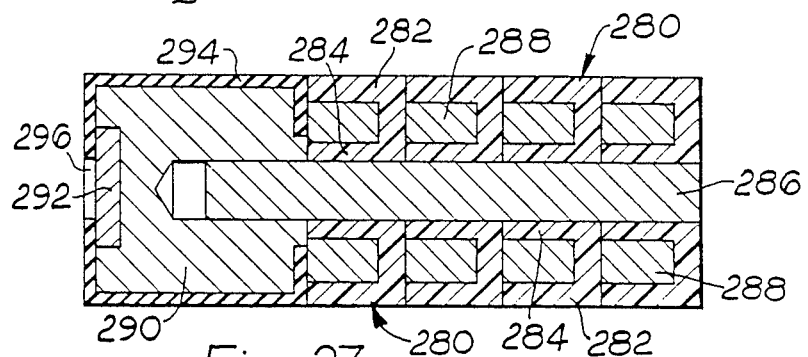
FIG. 27 is a longitudinal section illustrating yet a further embodiment of the bolus of the invention.

FIG. 27 of the drawings illustrates an embodiment of the bolus of the invention which is particularly suitable for use in sheep, in that it comprises components which may all either be degraded or corroded away, or be regurgitated or excreted so that in the long term no residue from the bolus remains in the treated animal. The bolus comprises outer segments 280 of a suitable liquid impervious material such as polyvinyl chloride which are C-shaped in radial cross-section so that they are of disc-like configuration providing an outer cylindrical portion 282 and an inner sleeve-like portion 284 whereby said inner sleeve portions are an interference fit on a central rod 286 of a magnesium alloy. The C-configuration of the segments 280 is such as to provide therein respective recesses accommodating respective inner ring-form segments 288 of a biologically active material. The outer segments 280 butt tightly up against one another so that the outer cylindrical portions 282 together provide a liquid impermeable casing of the bolus.

The central rod 286 projects beyond the endmost outer segment 280 at one end of the bolus and the projecting portion has thereon a weight 290 which is preferably of a zinc alloy and which is also an interference fit on the rod 286. At its face remote from the rod 286, the weight 290 is formed with a shallow recess which is occupied by a disc 292 of a noble metal such as stainless steel, which will form a galvanic couple with the magnesium rod 286 when the disc 292 and rod 286 are exposed to liquid such as the rumen juices of an animal, or water in a river or lake, effective to influence the rate at which the rod 286 is eroded away by the effect thereon of the liquid. The weight 290 is enclosed by an impermeable covering 294 except in register with the disc 292 whereat there is an opening 296 by which surrounding liquid can contact the disc 292 to enable the galvanic couple to arise.

In this embodiment use can be made of another noble metal for the disc 292 in the place of stainless steel. Moreover, it may not be essential for the weight 292 to be enclosed by the covering 294 because, in theory, the zinc alloy of the weight 292 should not be degraded until such time as the magnesium alloy rod 286, which behaves after the manner of a sacrificial anode, has corroded away. As will be appreciated, however, once the rod 286 has been consumed, the zinc alloy weight 290 will corrode away so that it will not remain within the dosed animal.

Figure 28:
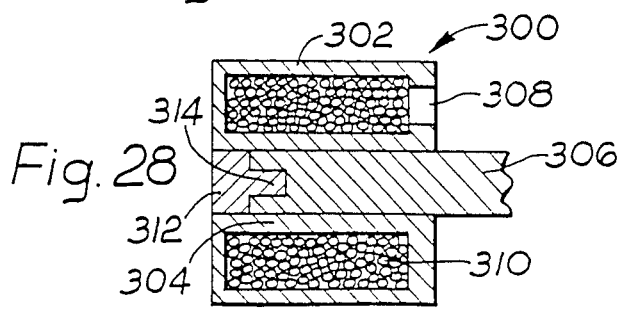
FIG. 28 is a fragmentary sectional view illustrating an alternative form of weight which may be used, for instance, in the place of the weight in the bolus of FIG. 27.

FIG. 28 illustrates a form of end weight 300 which may be used, for example, in the place of the weight 290 of the bolus of FIG. 27. In this construction, the weight 300 comprises a hollow annular shell 302 having a central sleeve 304 by which it fits onto central magnesuim alloy rod 306 and one end face of which has therein an opening 308 by which the shell 302 is filled with iron shot 310, the opening 308 being closed off by abutment of the shell 302 against the adjacent outer segment 282 or the active material segment 288 thereof. In this embodiment, a stainless steel plug 312 engages into the central sleeve 304 from the opposite end to that penetrated by the rod 306, this plug 312 engaging by a central spigot 314 into a complementary axial bore in the rod 306 and functioning in the same way as the disc 292 in the embodiment of FIG. 27.

With this arrangement, when the final biologically active segment 288 has been released, the shot 310 is able to leave the shell 302 and eventually the shot 310 and the shell 302 are either excreted or regurgitated, leaving no residue or fragments in the treated animal.

Figure 29:
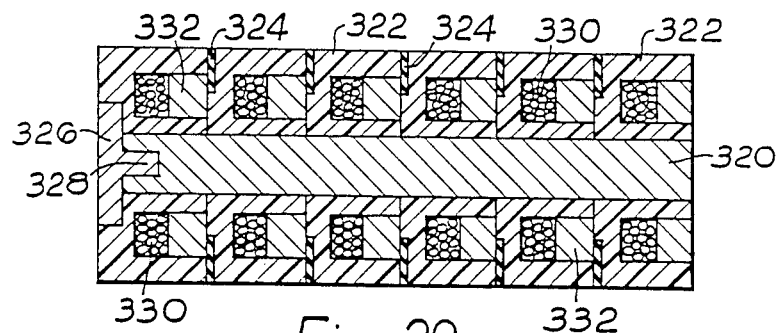
FIGS. 29 to 32 are longitudinal sections illustrating four further embodiments of the bolus of the invention.

The embodiment of the bolus of the invention illustrated in FIG. 29 is also of a form suitable for use in sheep. It comprises central rod 320 of a magnesium alloy on which are outer segments 322 which are similar in configuration to those of FIGS. 25 and 26 and are sealed relative to one another by sealing washers 324, being an interference fit on the rod 320 which has a stainless steel galvanic couple disc 326 engaging therewith by means of a spigot 328, the disc 326 being let into the endmost outer segment 322. Each segment 322 defines a respective annular recess which accommodates a respective annular weight 330 as well as a respective filling 332 (e.g. in the form of an annular tablet) of a biologically active material. Each weight 330 is, for example, of bonded iron shot, and each annular tablet 332 may be of such a composition that, after release of the tablet in the rumen, the composition is either immediately released or gradually released over a prolonged period of time.

When the bolus is spent, the segments 322, the disc 326 and the annular weights 330 should be expelled by the animal by excretion and/or regurgitation, the small size of the weights 330 permitting this.

An advantage of this embodiment lies in the fact that the overall density of the bolus, during its erosion, remains approximately constant in comparison with those embodiments where there is a single weight which is not corroded or degraded until the biologically active segments have been released and wherein the overall bolus density usually gradually increases.

Figure 30:
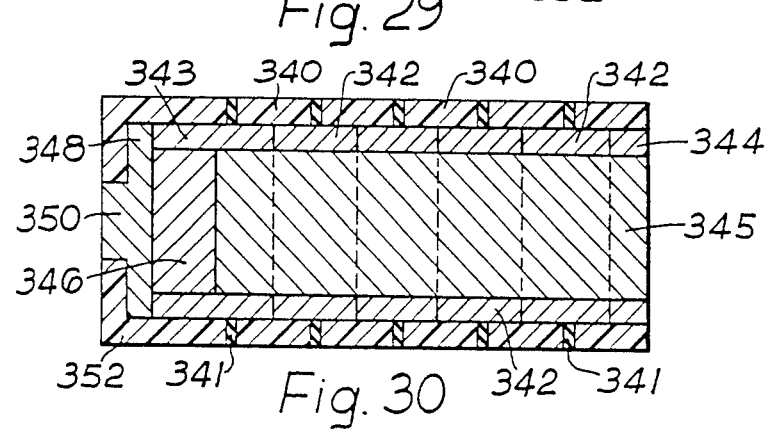

FIG. 30 serves to illustrate an embodiment of bolus according to the invention which again is suitable for administration to sheep. In this case, outer ring-form or tubular segments 340 of liquid impervious material surround ring-form or tubular inner segments 342, 343 and 344 of magnesium alloy, which in turn surround a central unitary core segment 345 of biologically active material. The axial lengths of the segments 340 and 342 is such that they overlap, being a relatively tight interference fit the one in the other with sealing washers 341 serving to seal the segments 340 relative to one another. Endmost inner segment 343 is of longer axial length than the segments 342 and accommodates both a part of the core 345 and a zinc alloy endweight 346 abutted by a galvanic couple disc 348. This disc 348 has a central protrusion 350 projecting through an opening in endmost outer segment 352 which covers the respective end of the bolus in a liquid impermeable manner.

Figure 31:
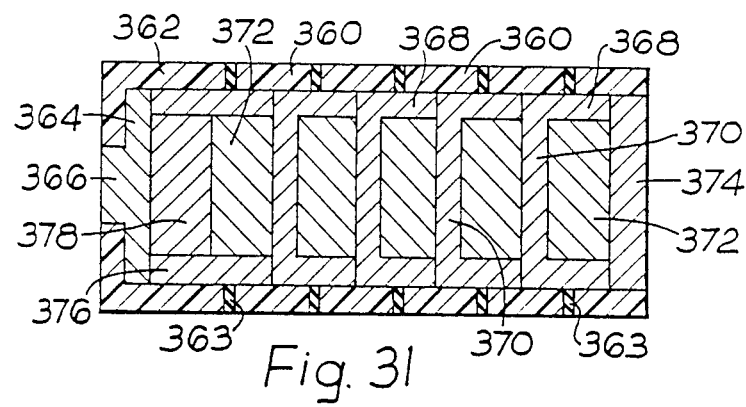

The embodiment of FIG. 31 is similar to that of FIG. 30 in that it comprises ring-form or tubular outer segments 360 and a longer outer segment 362 which encloses a galvanic couple disc 364 except at a central protrusion 366 thereof. These outer segments 360, 362, which are sealed relative to one another by silicone rubber washers 363, enclose a plurality of tubular magnesuim alloy inner segments 368 each of which is integral with a respective disc 370 and defines a respective recess accommodating a respective tablet 372 of biologically active material. At its end remote from the galvanic couple disc 364, the bolus is blanked off by a plain magnesium alloy disc 374 or an equivalent disc of wax or the like. Adjacent the disc 364, a plain tubular magnesium alloy segment 376 accommodates both a tablet 372 and a zinc alloy end weight 378. This embodiment of the bolus of the invention is used in the same way as that of FIG. 30. However, in contrast with the latter which serves to administer a continuous supply of the biologically active material to the treated animal, this embodiment is effective to administer pulsed doses.

When the bolus is spent, the end weight 378 is corroded away, whilst the galvanic couple disc 364 and the outer segments 360, 362 are regurgitated or excreted.

Figure 32:
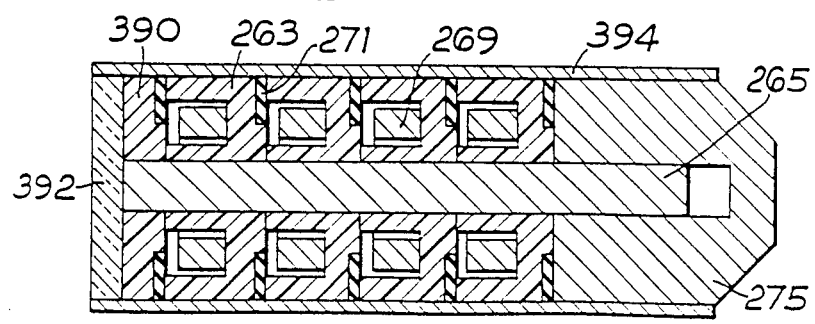

Finally, FIG. 32 illustrates an embodiment of the bolus of the invention which is basically similar to that of FIG. 26, and for the sake of convenience similar reference numerals have been used in this figure to denote those parts which are similar to those already described with reference to FIG. 26. There are, of course, in this embodiment only four annular segments 269, for example of oxfendazole, (although any desired number may be provided) and the endmost outer segment 263 remote from the end weight 275 is closed off by a plain polyvinyl chloride ring 390 abutted by a disc 392 consisting of a wax composition incorporating oxfendazole.

The outer segments 263, the end weight 275, the ring 390 and the disc 392 are enclosed in a rolled tube 394 of cardboard or paper, the rolling being of helical configuration which is conducive to the tube 394 peeling away after being wetted by rumenal fluids. This embodiment of the bolus provides an initial dose of oxfendazole immediately upon administration, from the wax disc 392. Shortly thereafter the tube 394 peels away and the bolus then corrodes away and administers pulsed doses in the same way as the embodiment of FIG. 26.

Instead of a wax composition, the disc 392 may be of any other suitable material, such as plaster of Paris, incorporating the oxfendazole, or any other appropriate biologically active material. If desired, the endmost polyvinyl chloride ring 390 may be exposed at the respective end of the tube 394 in which case the latter may extend beyond the end weight 275 and accommodate a disc similar to the disc 392 adjacent such end weight 275.

The paper tube 394 can, of course, be provided on any of the above-described embodiments.

In the boluses described above in relation to FIGS. 1 to 32, the therapeutic material may be any suitable form of biologically active material. For instance it may be an anti-coccidial composition, preferably of Lasalocid or M 139603 (defined above).

FORMULATIONS

An example of a formulation suitable for the biologically active inner segments of the above-described embodiments may, for instance, comprise an active ingredient in the form of an anthelmintic such as oxfendazole or an anti-coccidial such as Lasalocid or M 139603 (defined above), as follows:

|                      | Weight w/w |
|----------------------|------------|
| Active ingredient    | 75.0%      |
| Starch               | 10.0%      |
| PVP                  | 2.5%       |
| Magnesium Stearate   | 1.0%       |
| Lactose              | 11.5%      |

The active ingredient, starch and lactose are blended, then granulated with PVP solution in aqueous ethanol. The resultant granules are dried and mixed with the magnesium stearate lubricant and, finally, compressed into a tablet. For the devices of FIGS. 1 to 5, 15 and 16, the tablet is formed in a conventional disc shape, weighing for example 1 g with a diameter of about 15 mm and a thickness of about 5 mm. Such a disc shaped tablet may also be used for the device of FIGS. 6 and 7, although preferably, in this case, the tablet is in the shape of a disc having a chordal portion removed, the edge in that region then being generally flat. For the devices of FIGS. 8 to 13, i.e. devices having a central rod, the weight of the tablet preferably is 1 g and it is of annular shape with a thickness of about 5 mm and a diameter of about 19 mm, and a central hole of about 12.25 mm in diameter.

In the case of the devices shown in FIGS. 14, 21 and 30 the mixture is formed into a rod-like component of about 100 mm length, diameter about 17 mm, the weight being 80 g. This component forms the core of the device, in the device of FIGS. 14 and 21 and in FIG. 30 the core comprises the rod 345 and the inner magnesium alloy segments 342, 343, and 344.

We claim:

1. A release device in the form of a bolus of generally elongate configuration having two ends, said bolus comprising a liquid impermeable casing and a core surrounded by said casing and exposed at least at one of said two ends of the bolus, said core comprising a biologically active material and being degradable when the bolus is exposed to a liquid environment to release said material, and said casing comprising a plurality of outer segments which are successively shed from the bolus as said core is progressively degraded.

2. A release device as set forth in claim 1 wherein said outer segments are tubular segments of inert material.

3. A release device as set forth in claim 2 wherein said outer segments seal relative to one another by abutting against one another.

4. A release device as set forth in claim 3 further including a sealing washer between each adjacent pair of said outer segments.

5. A release device according to claim 1 wherein said biologically active material is Lasalocid comprising the formula 3-methyl-6-[7-ethyl-4-hydroxy-3,5-dimethyl-6-oxo-7-[5-ethyl-3-methyl-5-(5-ethyl-5-hydroxy-6-methyl-2-tetrahydropyranyl)-2-tetrahydrofuryl]heptyl]-salicyclic acid.

6. A release device as set forth in claim 1 wherein said biologically-active material is M139603 comprising the chemical structure of 2,3,4,5-tetrahydro-3-[(2S)-2-{(1S,2R,6S)--6-[(E)-2-]-(2R,3R,-6S)-6-[(E)-2-](2R,3R,6S)-3,4,5,6-tetrahydro-6-{(3S,E-3-{(2R,3S,5R)-2,3,4,5-tetrahydro-5-[(1S)-1-methoxyethyl]-3-methylfur-2-yl}-but-1-enyl}-3-methyl-2H-pyran-2-yl{-3-hyroxyprop-1-enyl]-2-methylcyclohexyl}propionyl]furan-2,4-dione, sodium salt).

7. A release device in the form of a bolus of generally elongate configuration having two ends, said bolus comprising a liquid impermeable casing and a unitary rod-form core surrounded by said casing and exposed at least at one of said two ends of the bolus, said core comprising a biologically active material and being degradable when said bolus is exposed to a liquid environment to release said material into said environment, and said casing comprising a plurality of outer segments which are successively shed from the bolus as said core is progressively degraded.

8. A release device in the form of a bolus of generally elongate configuration having two ends, said bolus comprising a liquid impermeable casing and a core surrounded by said casing and exposed at least at one of said two ends of the bolus, said core comprising a plurality of spaced-apart circular inner segments of biologically active material and being degradable when said bolus is exposed to a liquid environment to release said material, and said casing comprising a plurality of outer segments which are successively shed from the bolus as said core is progressively degraded.

9. A release device in the form of a bolus of generally elongate configuration having two ends, said bolus comprising a liquid impermeable casing and a core surrounded by said casing and exposed at least at one of said two ends of the bolus, said core comprising a plurality of spaced-apart annular inner segments of biologically active material penetrated by a rod, said inner segments and said rod being degradable when said bolus is exposed to a liquid environment to release said material, and said casing comprising a plurality of outer segments each having a respective flange extending inwardly to said rod thereby to space apart a respective pair of said inner segments, said outer segments being arranged to be shed from the bolus as said core is progressively degraded.

10. A release device as set forth in claim 9 wherein said rod is of magnesium alloy.

11. A release device as set forth in claim 9 wherein the said segments are retained relative to one another by the rod.

12. A release device in the form of a bolus of generally elongate configuration having two ends, said bolus comprising a liquid impermeable casing and a core surrounded by said casing and exposed at least at one of said two ends of the bolus, said core comprising first inner segments of a biologically active material, and second inner segments of metal, which may also be biologically active, separating said first inner segments, which first and second inner segments are degradable when the bolus is exposed to a liquid environment, to release said biologically active material, and said casing comprising a plurality of outer segments which are successively shed from the bolus as said core is progressively degraded.

13. A release device as set forth in claim 12 wherein said second inner segments are of magnesium alloy.

14. A release device as set forth in claim 12 wherein said biologically active material is selected from the group consisting of therapeutic agents, anti-coccidials, growth promotants, anthelmintics, insecticides and parasiticides.

15. A release device in the form of a bolus of generally elongate configuration having two ends said bolus comprising a liquid impermeable casing, a core surrounded by said casing and exposed at least at one of said two ends of the bolus, and means adapted to inhibit regurgitation by an animal dosed with the device, said core comprising a biologically active material and being degradable when the bolus is exposed to the rumen juices of a dosed animal to release said biologically active material, and said casing comprising a plurality of outer segments which are successively shed from the bolus as said core is progressively degraded.

16. A release device as set forth in claim 15 wherein said means adapted to inhibit regurgitation comprises weighting means effective to retain the bolus in the rumen of the dosed animal until the biologically active material of the core is spent.

17. A release device in the form of a bolus of generally elongate configuration having two ends, said bolus comprising a liquid-impermeable casing and a core surrounded by said casing and exposed at least at one of said two ends of the bolus, said core comprising a biologically-active material and being degradable when the bolus is exposed to a liquid environment to release said material and said casing comprising a plurality of outer finite unattached segments disposed in abutting liquid-tight sealing engagement with each other.

18. A release device in the form of a bolus of generally elongate configuration having two ends, said bolus comprising a liquid-impermeable casing and a core surrounded by said casing and exposed at least at one of said two ends of the bolus, said core comprising a biologically-active material and being degradable when the bolus is exposed to a liquid environment to release said material and said casing comprising a plurality of outer finite unattached segments provided with abutting flanges disposed in liquid-tight sealing engagement with each other.

19. A release device in the form of a bolus of generally elongate configuration having two ends, said bolus comprising a liquid-impermeable casing and a core surrounded by said casing and exposed at least at one of said two ends of the bolus, said core comprising a biologically-active material and being degradable when the bolus is exposed to a liquid environment to release said material and said casing comprising a plurality of outer finite unattached segments provided with interengageable edges disposed in sealing liquid-tight engagement with each other.

20. A release device in the form of a bolus of generally elongate configuration having two ends, said bolus comprising a liquid-impermeable casing and a core surrounded by said casing and exposed at least at one of said two ends of the bolus, said core comprising a biologically-active material and being degradable when the bolus is exposed to a liquid environment to release said material and said casing comprising a plurality of outer finite segments disposed end-to-end with sealing washers positioned therebetween in sealing liquid-tight engagement therewith.

* * * * *